United States Patent [19]
Shultz et al.

[11] Patent Number: 5,952,186
[45] Date of Patent: *Sep. 14, 1999

[54] REAGENT, METHOD, AND KIT FOR THE QUANTITATION OF OXIDATION-REDUCTION PHENOMENA IN PROTEINS AND PEPTIDES

[75] Inventors: John Shultz, Verona; Susanne Selman, Madison; Daniel J. Simpson, Middleton, all of Wis.

[73] Assignee: Promega Corporation, Madison, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/631,892

[22] Filed: Apr. 16, 1996

[51] Int. Cl.$^6$ .................................................. C12Q 1/00
[52] U.S. Cl. ............................ 435/7.9; 435/4; 435/113; 436/120; 548/126
[58] Field of Search .............................. 436/120; 435/7.9, 435/4; 548/113, 126

[56] References Cited

U.S. PATENT DOCUMENTS

| | | | |
|---|---|---|---|
| 4,374,928 | 2/1983 | Brot et al. | 435/68 |
| 5,605,809 | 2/1997 | Komoriya et al. | 435/23 |

OTHER PUBLICATIONS

Swadesh, J.K.; Mui, Philip W.; and Scheraga, Harold A., Thermodynamics of the Quenching of Tyrosyl Fluorescence by Dithiothreitol, *Biochemistry* (1987), vol. 26, pp. 5761–5769.

Evans, D.J., A Method for Determining the Penetration of Reducing Agents into Wool Using Fluorescence Microscopy, Textile Research Journal, Oct. 1989, pp. 569–576.

Baeyens, W.; Van der Weken, G.; and De Moerloose, P., Effects of Reducing Agents on the Determination of Thiolic Compounds in the Presence of their Disulfides Using Bimane Pre–Column Derivatization, *Chromatographia*, vol. 23, No. 10, Oct. 1987, pp. 717–721.

Reduction of N–Acetyl Methionine Sulfoxide: A Simple Assay for Peptide Methionine Sulfoxide Reductase, *Analytical Biochemistry*, 122: 291–294.

Held et al, Radiation Research, vol. 112, pp. 544–554, (1987).

Kosower et al, Biochimica et Biophysica Acta (BBA), vol. 622, pp. 201–209, (1980).

*Primary Examiner*—Ponnathapura Achutamurthy
*Assistant Examiner*—T. D. Wessendorf
*Attorney, Agent, or Firm*—DeWitt Ross & Stevens S.C.

[57] ABSTRACT

A first embodiment of the method is for analyzing the amount of methionine sulfoxide in a protein sample and includes the steps of contacting a protein solution with methionine sulfoxide reductase in the presence of a reducing reagent bearing a covalently-linked reporter tag, whereby the reducing reagent is oxidized. The oxidized reducing reagent formed, which is in proportion to the amount of methionine sulfoxide in the sample, is then quantified. A second embodiment of the method is for analyzing the amount of disulfide linkages in a polypeptide or protein sample. It proceeds in the same fashion as above, but in the absence of any enzyme. A novel fluorescently-labeled reducing agent, and kits to practice the method are also disclosed.

14 Claims, 4 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:1:

GAGCGACATC ATGAGTTTAT TTGATAAAAA           30

(2) INFORMATION FOR SEQ ID NO:2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:2:

CAACAATCTA CATTGGTACC CGTAACG              27

REAGENT, METHOD, AND KIT FOR THE QUANTITATION OF OXIDATION-REDUCTION PHENOMENA IN PROTEINS AND PEPTIDES

FIELD OF THE INVENTION

The present invention is directed to a novel method for quantifying oxidation-reduction phenomena in polypeptides and proteins which utilizes reductase enzymes and novel oxidatively-linked reducing reagents which include a reporter tag.

DESCRIPTION OF THE PRIOR ART

A major difficulty in the purification and storage of proteins is the covalent modification of the side chains of certain amino acid residues in the protein. In particular, the side chain of methionine is very susceptible to oxidation to methionine sulfoxide. This reaction takes place readily under the temperature and pH conditions normally used during the purification and storage of proteins. For this reason, many protein purifications are performed using buffers which contain a reducing reagent such as dithiothreitol (DTT) to prevent the oxidation of the protein.

In many instances, however, it is undesirable to have a reducing reagent such as DTT present with a protein in solution. For example, many proteins are stabilized by disulfide bonds between cysteine residues in the protein. Reagents such as DTT can reduce these bonds, thus causing an instability in the protein. In addition, the presence of a compound such as DTT is not permitted if the protein is to be used as a therapeutic agent. As a consequence it is not always possible to avoid the problem of methionine oxidation in proteins by adding a reducing reagent to the protein solution.

The oxidation of methionine to methionine sulfoxide has been reported in the scientific literature to inactivate several proteins. However, several additional and distinct reactions, such as deamidation, have also been reported to inactivate proteins. Thus, an accurate and sensitive test for the quantitation of methionine sulfoxide is needed to determine if the inactivation of a particular protein is due to oxidation of methionine residues within the protein or if the inactivation is caused by some other chemical reaction. For this reason there is a need for an accurate and sensitive test for the measurement of methionine sulfoxide residues in proteins and peptides.

Tests to measure methionine sulfoxide in a protein or peptide have been described. Some of these tests employ chemical reagents which react with methionine but not methionine sulfoxide. For example, cyanogen bromide reacts with methionine residues to form methyl cyanide, but cyanogen bromide does not react with methionine sulfoxide. Thus, one way to test for the presence of methionine sulfoxide in a protein sample is to react the protein with cyanogen bromide and then determine if the amount of methyl cyanide produced is equal to the amount expected from the reaction of cyanogen bromide with the protein. Unfortunately, this test is very difficult and cumbersome to perform for several reasons: (1) the reagents used are very toxic and volatile; (2) the methyl cyanide produced in the reaction is also very volatile and toxic; and (3) a by-product of the reaction is itself an oxidizing agent which is capable of oxidizing methionine to methionine sulfoxide. This creates difficulties in accurately quantitating the amount of methionine present in the sample. Additionally, the reaction takes several hours to perform.

An enzyme which is capable of reducing methionine sulfoxide to methionine is described in U.S. Pat. No. 4,374,928, to Brot and Weissbach. Here, the enzyme methionine sulfoxide reductase is used to reduce the protein L12 to a form which then acts as a substrate for other enzymes. During the reaction, the methionine sulfoxide reductase is reported to use disulfide reducing reagents such as thioredoxin or DTT as substrates to provide the reducing equivalents for the reaction. In theory, this assay can be modified to detect the presence of methionine sulfoxide in a sample by showing that less reduction of the oxidized form of L12 takes place in the presence of a sample than in the absence of a sample due to competition between the two substrates for reduction by the enzyme.

In fact, these researchers have produced a radioactive version of this assay which uses a radiolabelled form of acetyl methionine sulfoxide to determine the amount of reduced, radiolabelled acetyl methionine which is produced in the presence and absence of a sample which may contain methionine sulfoxide. (See Brot et al. (1982), Reduction of N-Acetyl Methionine Sulfoxide: A Simple Assay for Peptide Methionine Sulfoxide Reductase, *Analytical Biochemistry*, 122: 291–294.) However, none of the above methods are widely used today. This is largely due to the inherent inaccuracies caused by the use of a labelled methionine sulfoxide reductase substrate. The labelled enzyme substrate is used to determine if a sample contains methionine sulfoxide by reacting an amount of the labelled substrate with methionine sulfoxide reductase in the presence and absence of the sample and measuring the difference in the amount of substrate reduction. However, if the particular peptide which contains the methionine sulfoxide is itself a poor substrate for the enzyme, the assay requires a large amount of the peptide in the sample in order to cause a measurable decrease in the amount of the labelled substrate which is reduced. But, if the peptide which contains the methionine sulfoxide residue is a very good substrate for the enzyme, the assay will function acceptably with a lower concentration of the peptide being assayed. This effect makes quantitation of the amount of methionine sulfoxide in the sample almost impossible to determine solely by determining a reduction in the labelled product of the reaction because the suitability of the peptide as an enzyme substrate also plays an important role in the enzymatic reduction. In addition, accurate determination of the relative amounts of labelled product produced cannot occur if the sample contains substances which inhibit the reductase enzyme, but which do not contain methionine sulfoxide. For example, if a sample contains a compound which denatures the reductase enzyme, the sample will decrease the amount of labelled methionine sulfoxide product which is produced even if the sample contains no methionine sulfoxide. This effectively destroys the utility of such an assay.

The present invention overcomes the difficulties with the assay methods known in the prior art by utilizing a novel assay methodology which does not suffer from the limitations inherent in the above-described methods. None of the above references, taken alone or in any combination, describe or suggest the invention disclosed and claimed herein.

SUMMARY OF THE INVENTION

In light of the above discussion, a first embodiment of the present invention is drawn to a method to determine the amount of methionine sulfoxide in a sample. The method comprises the steps of contacting the sample with a methionine reductase in the presence of a reducing reagent which includes a covalently-linked reporter tag. Methionine sulfoxide in the sample is thereby reduced and a proportional amount of the reducing reagent is oxidized. The amount of oxidized reducing reagent is then quantified using detection means which are responsive to the reporter tag.

A second embodiment of the present invention is directed to a method to determine the amount of disulfide linkages in a sample. This second embodiment comprises the steps of contacting the sample with a reducing reagent which includes a covalently-linked reporter tag, as described above. Disulfide linkages in the sample are thereby reduced and a proportional amount of the reducing reagent is oxidized. The amount of oxidized reducing reagent is then quantified using detection means which are responsive to the reporter tag.

A third embodiment of the present invention is drawn to a kit for quantifying methionine sulfoxide in a sample. The kit includes, in combination: a methionine sulfoxide reductase enzyme disposed in a first container, a reducing reagent including a covalently-linked reporter tag disposed in a second container, and instructions for use of the kit.

A fourth embodiment of the invention is drawn to a related kit for quantifying disulfide linkages in a sample. This kit includes, in combination: a reducing reagent including a covalently-linked reporter tag disposed in a first container, a stop reagent disposed in a second container, and instructions for use of the kit.

A fifth embodiment of the present invention is directed to a composition of matter comprising dithiothreitol covalently linked through at least one of its two hydroxyl moieties to a fluorescent substituent.

A sixth embodiment of the present invention is drawn to a fluorescent compound having a structure as shown in Formula I when reduced and a structure as shown in Formula II when oxidized:

FORMULA I (Reduced Form)

FORMULA II (Oxidized Form)

A seventh embodiment of the present invention is drawn to a method to determine the presence and concentration of metal dissolved in a sample. The method comprises contacting the sample with a reagent which includes a covalently-linked reporter tag, wherein the reporter tag emits a signal which is quenched in proportion to the amount of metal dissolved in the sample. The signal emitted by the reporter tag is then quantified using detection means responsive to the reporter tag, whereby the presence and concentration of dissolved metal in the sample can be determined.

It is a principal aim of the present invention to provide a method to evaluate the presence of methionine sulfoxide in polypeptides and proteins utilizing peptide methionine sulfoxide reductase enzymes and novel labelled, oxidatively-coupled reducing reagents. The method is rapid, accurate, and reproducible. The method is also enhanced by performing it in the presence of thioredoxin.

Another aim of the present invention is to provide a method to quantify the amount of methionine sulfoxide present in a sample utilizing the above-described methionine sulfoxide reductase and novel reducing reagents, as well as a stop reagent.

It is a further aim of the present invention to provide a method to quantify the amount of disulfides present in a sample utilizing the above-described novel reducing reagents.

A still further aim of the present invention is to provide a method to determine the presence and concentration of dissolved metal in a sample.

Another aim of the present invention is to provide self-contained kits containing the necessary reagents to perform the above methods.

Yet another aim of the present invention is to provide novel compositions of matter including a reducing agent and a reporter moiety covalently attached thereto.

In each of the above methods, it is preferred that the reducing reagent is dithiothreitol which has been modified to include a covalently-linked reporter tag. It is preferred that the reporter tag be a fluorophore. The fluorophore can be any number of widely known fluorophores such as fluorescein and fluorescein-based fluorphores (e.g., carboxyfluorescein diacetate succinimyl ester, fluorescein isothiocyanate, etc.), rhodamine-based fluorophores (e.g., TEXAS RED and tetramethylrhodamine isothiocyanate), dansyl, and NBD (i.e., 6-(7-nitrobenz-2-oxa-1,3-diazol-4-yl) aminohexanoate). NBD is preferred.

Several advantages are realized by the present invention. Among these advantages are speed, ease, and safety. Compared to prior art methods, the method described therein is far more rapid.

The methodology described herein is easy to perform using readily available reagents and equipment. The reagents used in the present invention are far less toxic and volatile than those used in the prior art, which obviates the need for cumbersome handling and storage precautions. This also makes the present methodology far safer than prior art methods. The method described herein does not require the use of, or result in the formation of, cyanide compounds. Nor does the present method require the use of radioactive reagents.

Another tremendous advantage of the present invention is its flexibility, accuracy, and precision. Because the method does not result in the formation of by-products which add extraneous oxidative or reductive potential to the reaction milieu, the present method is far more accurate and precise than prior art methods. The present method can also be used to evaluate several oxidation-reduction phenomena in protein solutions. As noted above, the present method can be used to determine the amount of methionine sulfoxide in a polypeptide or protein. The method can also be used to determine the amount of disulfide linkages in a protein.

These and other aims, objects, and advantages of the present invention will become clear upon a complete examination of the Detailed Description, drawing figures, and claims, below.

BRIEF DESCRIPTION OF THE DRAWINGS

FIG. 1: An image of the detected fluorescent materials present on the TLC plate described in Example 6 is shown. The samples fractionated in the various lanes are: Lane 1—reaction 1, sample taken at time (t)=0 min; Lane 2—reaction 2, sample taken at t=0 min; Lane 3—reaction 1, sample taken at t=1 min.; Lane 4—reaction 2, sample taken at t=1 min; Lane 5—reaction 1, sample taken at t=2 min; Lane 6—reaction 2, sample taken at t=2 min; Lane 7—reaction 1, sample taken at t=3 min; Lane 8—reaction 2, sample taken at t=3 min; Lane 9—reaction 1, sample taken at t=4 min; Lane 10—reaction 2, sample taken at t=4 min; Lane 11—reaction 1, sample taken at t=5 min; Lane 12—reaction 2, sample taken at t=5 min; Lane 13—reaction 3, sample taken at t=0 min; Lane 14—reaction 3, sample taken at t=1 min; Lane 15—reaction 3, sample taken at t=2 min; Lane 16—reaction 3, sample taken at t=3 min; Lane 17—reaction 3, sample taken at t=4 min; Lane 18—reaction 3, sample taken at t=5 min; Lane 19—reaction 4, sample taken at t=0 min; Lane 20—reaction 5, sample taken at t=0 min; Lane 21—reaction 4, sample taken at t=1 min; Lane 22—reaction 2, sample taken at t=1 min; Lane 23—reaction 4 sample taken at t=2 min; Lane 24—reaction 2, sample taken at t=2 min; Lane 25—reaction 4 sample taken at t=3 min; Lane 26—reaction 5, sample taken at t=3 min; Lane 27—reaction 4, sample taken at t=4 min; Lane 28—reaction 5, sample taken at t=4 min; Lane 29—reaction 4, sample taken at t=5 min; Lane 30—reaction 5, sample taken at t=5 min; Lane 31—reaction 6, sample taken at t=0 min; Lane 32—reaction 6, sample taken at t=1 min; Lane 33—reaction 6, sample taken at t=2 min; Lane 34—reaction 6, sample taken at t=3 min; Lane 35—reaction 6, sample taken at t=4 min; Lane 36—reaction 6, sample taken at t=5 minutes. The mobility of the oxidized form of the methionine substrate is indicated by the single arrow; the mobility of the reduced form of the methionine substrate is indicated by the double arrow.

FIG. 2: An image of the detected fluorescent materials present on the TLC plate described in Example 7 is shown. The samples fractionated in the various lanes are: Lane 1—reaction 1: 1 μl spotted without NEM addition; Lane 2—reaction 1: 2 μl spotted after NEM addition; Lane 3—reaction 2: 1 μl spotted without NEM addition; Lane 4—reaction 2: 2 μl spotted after NEM addition; Lane 5—reaction 3: 1 μl spotted without NEM addition; Lane 6—reaction 3: 2 μl spotted after NEM addition; Lane 7—reaction 4: 1 μl spotted without NEM addition; Lane 8—reaction 4: 2 μl spotted after NEM addition; Lanes 9–16: duplicates of lanes 1–8, respectively—the left-pointing arrow indicates the spot which represents the NEM modified-NBD modified REDUCED DTT; Lanes 17 and 18—standard containing NBD-modified reduced DTT (upper spot, indicated by single arrow) and NBD-modified oxidized DTT (second spot, indicated by double arrow).

DETAILED DESCRIPTION OF THE INVENTION

The present invention is directed generally to a method for evaluating oxidation-reduction phenomena in solutions containing polypeptides or proteins. A first embodiment of the present invention is directed to measuring the oxidation of methionine residues in proteins. This first embodiment of the invention measures the amount of methionine sulfoxide residues in a protein or peptide through the use of the enzyme methionine sulfoxide reductase and a novel fluorescently-labelled reducing reagent. The assay allows for the amount of methionine sulfoxide present in a sample to be easily measured by determining the amount of oxidized labelled reducing reagent produced in the reaction. The present assay does not depend upon competition between enzyme substrates to determine the amount of methionine sulfoxide in a sample. Analogous embodiments of the present invention which do not require enzymatic reduction are also described below.

Surprisingly, the labelled form of the reducing reagent described herein is easily utilized by the reductase enzyme, thus allowing the reaction between the enzyme and the sample to be performed in as little as 5 minutes at room temperature. This compares very favorably with the long reaction times required (at least several hours) in the methods known in the prior art.

More surprisingly still, as detailed below, the amount of labelled reagent needed to perform the method can be decreased over 100-fold in reactions which contain trace amounts of another protein, thioredoxin. This result is very advantageous because it allows for the use of very low concentrations of the labelled reagent. This allows a much larger fraction of the reducing reagent to be converted to the oxidized product. In turn, the large fraction of oxidized product simplifies the accurate measurement of the amount of oxidized product by attenuating or entirely eliminating the signal produced by unreacted reagent.

In other words, by decreasing the amount of reagent needed, a greater proportion of the reagent is converted into its oxidized form during the course of the reaction. This increases the relative signal strength from the oxidized product as compared to the unreacted reagent. As an illustration, the concentration of DTT reducing reagent needed to support the reaction, as measured by the $K_m$ for either labelled or unlabelled DTT, is around 3 mM. If the reagent were used at this concentration (3 mM) to measure the amount of methionine sulfoxide in a 100 pico-mole (pmole, i.e., $1 \times 10^{-12}$ mole) sample of protein, where the equivalent of 1 methionine residue per polypeptide chain had been oxidized to methionine sulfoxide, and further if the reaction were performed in a 100 μl volume, only 1 part in 3000 (0.03%) of the reducing reagent would be converted into its oxidized form by the action of the enzyme. The signal from such a small amount of material would be easily masked by atmospheric oxidation of the reagent or by small amounts of impurities present in the reaction. Since it is not unreasonable to use a 100 pmole sample in certain applications, it would be very difficult to distinguish the signal from the background noise.

In addition, in most instances only a small percentage of the sample is oxidized, normally only 2%–5%. In this instance, the signal generated from the reaction drops to approximately 1 part in 100,000, which makes the background signal generated from other reactions even more difficult to overcome.

The addition of thioredoxin to a reaction containing only 10 μM concentrations of a labelled DTT (a 300-fold decrease in DTT concentration) allows the reaction to proceed at a rate even faster than is seen in the absence of thioredoxin but using 3 mM solutions of the modified reagent. The ability to lower the concentration of the labelled reducing reagent at least 300-fold without dramatically slowing the reaction allows a much greater fraction of the reagent to be converted at both high oxidation levels (e.g., 1 part in 10 using 10 μM solutions with traces of thioredoxin versus 1 part in 3000 for the use of 3 mM solutions without thioredoxin) and low oxidation levels (e.g., 1 part in approximately 300 using 10 μM solutions with trace thioredoxin versus greater than 1 part in 100,000 for the use of 3 mM solutions of the reagent). In addition, decreasing the amount of labelled reducing reagent slows the background oxidation of the material by atmospheric oxygen, thus improving the ruggedness of the assay.

Additionally, the fluorescence signal of the reduced form of the reagent can be greatly attenuated by the addition of small amounts of metal salts to the reaction solution. The oxidized form of the reagent is relatively insensitive to the presence of the metal salts. Consequently, to measure the amount of oxidized reagent produced in the reaction is a simple matter of adding a metal salt to the reaction products and measuring the residual fluorescence of the solution. This effect eliminates the need to separate the oxidized and reduced forms of the reagent prior to measuring their respective signal strength.

The present invention also includes an effective reagent for terminating the reaction (designated herein as a "stop reagent") which stabilizes the chemical entities formed so that the analysis of the amount of oxidized and reduced reagent present at the end of the reaction can be determined following separation of the reaction products.

For the sake of brevity and clarity, the following discussion is limited to a discussion regarding the use of methionine sulfoxide reductase (MSR) and a modified dithiothreitol reducing agent (mDTT) to quantify the amount of methionine sulfoxide residues in a polypeptide or protein sample. The discussion which follows applies with equal validity to the other embodiments described herein which employ reactions that use the oxidatively-coupled reducing reagent alone. The discussion is so limited for the sake of brevity and clarity only, and does not limit the scope of the invention disclosed or claimed herein in any fashion.

In performing the first embodiment of the present invention, the enzyme methionine sulfoxide reductase (MSR) is purified to a high degree of purity as is known in the prior art. (See, for instance, Brot et al. (1981), Enzymatic Reduction of Protein-Bound Methionine Sulfoxide, *Proc. Natl. Acad. Sci.* 78(4): 2155–2158, incorporated by reference herein in its entirety.) Preferably, the enzyme is purified from *E. coli*. More preferable still, the enzyme is expressed as an active enzyme from a cloned source of the enzyme produced in *E. coli*. The purification of the MSR can be performed using one of several methods well known in the art, such as salt precipitation using ammonium sulfate followed by fractionation of the protein solution over a number of different resins normally used for protein purification. (See, for instance, *Current Protocols in Molecular Biology* (1995) Vol. 2, Ch. 10, John Wiley & Sons, Inc., incorporated herein by reference.)

It has been found that the MSR enzyme is very conveniently purified from a recombinant *E. coli* host strain which over-expresses the protein from a cloned gene which encodes MSR. Construction of a suitable recombinant *E. coli* strain is described in full detail by Rahman et al. (1992), High Level Expression and Purification of Peptide Methionine Sulfoxide Reductase in *E. coli, Cell. and Mol. Biol.*, 38(5): 529–542, incorporated herein by reference in its entirety.

The reducing reagent preferably contains two sulfhydryl groups such as those in DTT or thioredoxin. Additionally, reagents containing a single sulfhydryl group, such as β-mercaptoethanol, can also be used with equal success. It is preferred that the reducing reagent be modified by the addition of a covalently linked reporter tag. The reporter tag is preferably a fluorophore. However, other detection methods, such as employing the absorptive properties of a reporter tag or of the reagent itself can be used. A wide variety of fluorescent reporters can be used. The preferred fluorophore is NBD (6-(7-nitrobenz-2-oxa-1,3-diazol-4-yl) aminohexanoate). A large number of diverse fluorophores are commercially available from several national suppliers, for instance, ICN Biomedicals (Costa Mesa, Calif.). Selection of the preferred fluorescent moiety to use will be at the discretion of the user with the caveat that the fluorophore tag must: 1) remain stable in aqueous solution; 2) be detectable in relatively low concentrations; and 3) be unreactive with sulfhydryl groups. Information regarding the chemical properties of fluorescent reporter tags is readily available to those skilled in the art.

The assay is initiated by incubating a sample which contains a protein or peptide to be tested with the methionine sulfoxide reductase (MSR) enzyme and the labelled reducing reagent under conditions where the MSR is capable of carrying out its enzymatic reduction. A reagent blank is also assembled. The blank includes the same materials as in the sample test, but the sample itself is replaced with an equivalent solution which does not contain the protein or peptide being tested. These conditions are well known to workers in the art and, in general, include incubating the reagents at neutral or near-neutral pH levels and at temperatures between about 0° C. and 37° C. It is preferred that the incubations are performed between about pH 5.5 and 9.0 and at temperatures between about 4° C. and 24° C.

The modified reducing agent, preferably NBD-tagged DTT, provides the reductive potential to drive the MSR-catalyzed reduction of methionine sulfoxide residues in the sample to methionine. (In reactions which do not require an enzyme, the tagged DTT directly reduces the species being assayed.) Simultaneously, the DTT portion of the reducing reagent is itself oxidized from its dithiol form to a disulfide form. The reduced and oxidized forms of the NBD-tagged DTT are shown below as Formula I and Formula II, respectively:

FORMULA I-Reduced form of NBD-tagged DTT (dithiol)

-continued

FORMULA II-Oxidized form of NBD-tagged DTT (disulfide)

Following incubation of the sample and the reagent blank, the reactions are terminated, preferably by the addition of a stop reagent, and the amount of oxidized labelled reagent present in the sample and the reagent blank, respectively, is determined. The difference between the amount of oxidized reagent in the sample run and the amount of oxidized reagent in the blank run is then calculated. This value is proportional to the amount of methionine sulfoxide in the sample. If the amount of protein in the sample is precisely known, the average number of methionine sulfoxide residues per polypeptide chain can also be determined.

If the reaction products are to be separated prior to quantitation, it is preferred, but not essential, that the reaction products be stabilized by addition of a stop reagent. Preferred stop reagents include bromoacetic acid, 5,5'-dithionitro-bis(2-nitrobenzoic) acid (also known as Ellman's Reagent or DTNB) and N-ethylmaleimide (NEM). These compounds effectively quench further redox reaction without affecting the fluorescent reactions used to detect the extent of reaction. Although DTNB is known to modify —SH groups, DTNB has been shown to have no deleterious effects on the modified DTT described herein.

Separation of the reaction products and unreacted reagents can be performed by techniques well known in the art, such as chromatography. Preferably, separation is accomplished via normal or reverse-phase chromatography. More preferably still, reverse-phase chromatography using high performance liquid chromatography (HPLC) equipment and column resins containing octyldecyl-modified silica is used to separate the reaction components. Modified silica resins can be obtained from several national suppliers, for instance, Millipore Corporation (Marlborough, Mass.).

If the signal measurement is to be performed fluorescently following the addition of metal salt, a stop reagent need not be used. The preferential signal quenching caused by the addition of the salt may also make it unnecessary to separate the reaction products from the reactants. It may be preferred that the separation be eliminated by the addition of the metal salt because it eliminates one step of the method, thereby making the method even faster and easier to perform. It is preferred that the metal salt be selected from the group consisting of $FeCl_3$, $MgCl_2$, $MnSO_4$, $NiSO_4$, RbCl, $CuSO_4$, $CuCl_2$, $CoCl_2$, $CsCl_2$, $CaCl_2$, and $ZnCl_2$.

An unexpected benefit of the preferential signal quenching is that the method can be modified to detect the presence and concentration of metal in a sample. Here, the reduced form of the NDB-modified DTT is added to a sample and the fluorescence is measured. The sample signal is then compared to a standard curve constructed from a series of control solutions. Because the fluorescent signal from the reduced form of the NBD-modified DTT is greatly attenuated by the presence of dissolved metals, the presence and concentration of dissolved metal in the sample can be determined by comparing any attenuation of the sample signal to the standard curve.

As described above, the assay is useful for determining the amount of methionine sulfoxide present in a protein or peptide sample. Such measurements are useful to define storage or purification conditions which prevent the protein or peptide of interest from being oxidized. The test method is useful for practically all proteins or polypeptides which contain a methionine residue because all proteins containing methionine are susceptible to oxidation of the methionine residue to methionine sulfoxide.

In a second embodiment of the invention, the labelled DTT reducing agent is utilized directly to determine the amount of disulfide linkages in a polypeptide or protein sample. The methodology of the second embodiment of the invention is substantially identical as that described above for MSR, with the exception that no enzyme is required.

Here, a sample is incubated in the presence of a modified reducing reagent including a reporter tag. The amount of reducing reagent which is oxidized during the incubation is then quantified via means responsive to the reporter tag. A stop agent, as described above, may be utilized to quench the reaction prior to measuring the reporter signal. As above, a fluorophore reporter is preferred. The amount of oxidation of the reducing agent provides data which allow the amount of disulfide linkages in the sample to be deduced as described above for methionine sulfoxide. Rather than separating the products of the incubation prior to measuring the fluorophore signal, it may be preferred that a metal salt, as described above, is added to the solution prior to measuring the fluorescence of the solution.

The present invention is also drawn to kits which contain all of the necessary reagents and instructions to carry out the above methods. The kit includes, in combination, a reductase enzyme, preferably a methionine sulfoxide reductase, disposed in a first container, an oxidatively-coupled reducing reagent including a covalently-linked reporter tag disposed in a second container, and instructions for use of the kit. Additionally, the kit may also include a stop reagent disposed in a third container, thioredoxin disposed in a fourth container, and a metal salt disposed in a fifth container. Preferably, the reducing reagent is NBD-tagged DTT.

The present invention is also drawn to fluorescent reducing agents, namely dithiothreitol having one or more fluorophores covalently linked to one or more of its two hydroxyl moieties. This covalent link is preferably an ester link, although other covalent linkages, such as ether links, are also contemplated. One compound of particular note is NBD-tagged dithiothreitol having the structure shown in Formula I in its reduced form, and the structure shown in Formula II when oxidized:

FORMULA I

-continued

FORMULA II

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Cloning of Gene Encoding E. coli Peptide Methionine Sulfoxide Reductase

The cloning of the gene encoding E. coli Peptide Methionine Sulfoxide Reductase was performed in a manner very similar to published protocols. (See, for instance, M. A. Rahman, et al. (1992), Cloning, Sequencing, and Expression of the E. Coli Peptide Methionine Sulfoxide Reductase Gene, *J. Biol Chem.*, 267(22): 15549–15551; and M. A. Rahman, et al. (1992), High Level Expression and Purification of Peptide Methionine Sulfoxide Reductase Gene, *Cell. Mol. Biol.*, 38(5): 529–542, both of which are incorporated by reference herein in their entirety.) The DNA from Lambda phages Kohara 656 and 657 were prepared using WIZARD LAMBDA DNA Prep (Promega Corp. Madison, Wis.). These preparations gave a DNA yield of 170 ng/μl and 180 ng/μl for the 656 and 657 phages, respectively. An amplification reaction was assembled using: 850 ng of lambda DNA; 50 pmole each of primers GAG CGA CAT CAT GAG TTT ATT TGA TAA AAA (SEQ ID NO: 1) and CAA CAA TCT ACA TTG GTA CCC GTA ACG (SEQ ID NO: 2); 2 mM MgSO$_4$ (final concentration); 0.05 mM each of dATP, dTTP, dCTP, and dGTP (final concentration); Promega Mg-free Taq buffer sufficient to produce 50 μl of a 1× concentration solution and 3 units of TLi DNA Polymerase (Promega Corporation, Madison, Wis.).

The reactions were then transferred to a Perkin Elmer 480 thermocycler (Ser. No. P10137) and amplifications were performed using the following temperature pattern: initial heating at 96° C. for 2 min, followed by 10 temperature cycles at 94° C. for 1 min, 55° C. for 1 min, and 70° C. for 1 min. After the cycling reactions, the reaction mixture was fractionated on an 1% TBE high melting point agarose gel. The reaction mixture was electrophoresed and then stained with ethidium bromide and visualized on a transilluminator as described in Maniatis et al. (Sambrook, Fritsch and Maniatis, "Molecular Cloning—A Laboratory Manual, Second Edition," Cold Spring Harbor Laboratory Press, (1989), incorporated herein by reference.) The reactions were shown to have produced a large amount of product at a molecular size of approximately 675 base pairs as expected from the prior art. The DNA fragment of approximately 675 base pairs was excised from the gel and isolated using Promega's WIZARD PCR Prep utilizing the protocol indicated for isolation of DNA from high melting point agar gels given in Promega Technical Bulletin 118 (revised version December 1993, incorporated herein by reference).

The isolated DNA was cut with BspHI (New England Biolabs, Beverly, Mass.) and Acc65I as described in Maniatis et al. (supra) and re-isolated using the Wizard PCR prep protocol indicated in the above paragraph. The isolated DNA was then inserted into a plasmid vector digested with enzymes to produce compatible DNA ends to those generated by BspHI and Acc65I. The plasmid is very similar to pKK223 from Pharmacia Corporation, which can be substituted if desired. The essential characteristics for the plasmid are: 1) that it carry the gene for tetracycline resistance from plasmid pBR322; 2) that it be a relatively high copy plasmid; and 3) that it also contains a Taq promotor oriented to transcribe the inserted gene for the peptide methionine sulfoxide reductase gene. The ligation was performed as described in Maniatis et al. and was allowed to proceed for 16 hours at 16° C. The resulting ligated DNA was then used to transform competent E. coli cells JM109 (high competency) from Promega Corporation.

The transformation mixture was performed by mixing 10 μl of the reaction mixture with 200 μl of the competent cells, which had been slowly thawed on ice. The mixture was incubated for 30 min on ice and then the bacteria heat shocked for 50 sec at 40° C. One ml of SOC broth (Maniatis et al.) was added to the cells and the cells were allowed to recover for 1 hr at 37° C. Samples of the resulting cell mixture were spread on LB Agar plates containing 12.5 μg of tetracycline per ml of agar mixture. The plates were allowed to absorb the added bacterial culture and were then incubated overnight at 37° C.

The following day, numerous tetracycline-resistant bacterial colonies were found to be growing on the plate. Ten of these colonies were streaked onto fresh plates of LB agar containing 12.5 μg of tetracycline per ml of agar mixture and incubated at 37° C. overnight. Samples of the heaviest portion of the streaked bacterial isolates were gathered using a sterile toothpick and the bacteria used for plasmid DNA isolation using WIZARD DNA miniprep materials and protocols as supplied by Promega.

The ten cultures all provided good amounts of plasmid DNA to be isolated. Samples of these DNA's were digested with DraI and Acc65I (Promega) and the reaction mixtures analyzed by electrophoresis on a 1% agarose gel as described above. The DNA bands were visualized following ethidium bromide staining. Nine of the digestions were shown to produce DNA fragments of approximately 650 and 4500 base pairs as expected for the desired clones. The strain which was used for isolation of one of the DNA preparations which produced the expected DNA fragment pattern was designated MSR-17 and was used for the over-expression of the plasmid methionine sulfoxide reductase protein, as described hereinbelow.

The DNA which was inserted into the plasmid isolated in strain MSR-17 was determined by DNA sequence analysis using the FEMTOMOLE DNA sequencing system of Promega Corp. Analysis of the data obtained indicated that the inserted DNA was identical in sequence to previously published sequences of the peptide methionine sulfoxide reductase gene of E. coli. In addition, the sequence of the gene was shown to be oriented in the plasmid such that induction of the taq promotor in the plasmid will drive transcription of the correct strand of the gene to express the peptide methionine sulfoxide reductase gene.

Example 2

Over-expression of Gene Encoding the Peptide Methionine Sulfoxide Reductase of E. coli A colony of strain MSR-17, described in Example 1, which was freshly grown on LB Agar containing 12.5 μg of tetracycline per ml overnight at 37° C. was transferred to 50 ml of L broth containing 10 μg of tetracycline per ml of media and grown at 37° C. with 200 rpm agitation to aerate the culture. When the bacterial culture reached a density of 0.1 OD at 600 nm, the culture was allowed to cool to 25° C. with continued agitation. When the culture achieved a OD of 0.6 at 600 nm, IPTG was added from a 200 mM filter-sterilized IPTG stock to a final concentration of 2 mM IPTG. Samples of the cells were taken immediately upon addition of the IPTG, and at 4, 9, and 20 hours after IPTG addition. The samples were centrifuged for 5 minutes in a microfuge immediately upon sampling of the cultures and frozen at −20° C. for subsequent analysis.

The cell pellets were resuspended in 100 μl of 1× Laemmli Sample buffer with gentle vortexing. The resuspended cells were heated at 95° C. to lyse the bacteria and solubilize the proteins in the sample. Portions of these lysates were fractionated using SDS PAGE electrophoresis on a 4–20% polyacrylamide gel for protein fractionation (Novex Corporation). The gel was run at 150 V until the tracking dye in the Sample Buffer reached the bottom of the gel. The gel then was stained using COOMASSIE BRILLIANT BLUE. Following destaining, the samples obtained from the culture containing IPTG were shown to include a protein species of approximately 30 kDa which was much greater in amount than in samples of the culture taken just prior to IPTG addition or in samples of the *E. coli* JM109 which did not contain the plasmid encoding the cloned gene.

Example 3

Purification of Methionine Sulfoxide Reductase

Cells expressing the gene encoding the peptide methionine sulfoxide reductase of *E. coli*. were grown as described in Example 2 with the exception that several cell cultures were grown in 1 L volumes of LB broth containing 10 μg of tetracycline per ml of broth in 3 L Fembach flasks, and inoculation of the culture was performed by addition of 10 ml of culture of the strain grown at 37° C. overnight in 50 ml of LB broth containing 10 μg of tetracycline per ml which had been inoculated from a stock of bacterial strain MSR-17. The bacteria in these cultures were isolated by centrifugation at 10,000×g for 15 minutes following 6 hours of growth after IPTG addition. A portion of these cells (9.7 g) was dissolved in 19.4 ml of 20 mM Tris (pH 7.5), 5 mM DTT, 100 mM NaCl and 1 mM PMSF (phenylmethylsulforyl-fluoride) at 4° C. while stirring by use of a magnetic stirrer and a magnetic stir bar for approximately 15 min to resuspend the cells. After a uniformly resuspended cell solution was obtained, 0.15 mg of lysozyme (Sigma Chemical Co., St. Louis, Mo.) was added per ml of suspension and the solution stirred at 4° C. for 2 hours. After the two hour incubation, $MgCl_2$ and $CaCl_2$ was added to the solution to a final concentration of 6 and 10 mM respectively. Then 1 μg of DNase (Promega Co., M601A Lot #4296615) was added per ml of suspended cell solution. The solution was then stirred for 1 hour at 4° C. This solution is referred to herein as the crude cell lysate.

The crude cell lysate was centrifuged at 21,000×g for 30 minutes at 4° C., the pellet discarded, and the supernatant dialyzed twice against 4 liters of a solution of 1 mM potassium phosphate, 10 mM Tris, 2.5 mM DTT, and 0.1 mM PMSF (pH 7.5). The first dialysis was run for 2 hours and the second dialysis was run overnight.

The solution was then centrifuged at 21,000×g for 10 minutes at 4° C. to remove any precipitated protein which may have formed during the dialysis.

A portion of the solution was then applied to an 8 ml column of hydroxyapatite (BioRad 157-0800 Lot 124078A, Hercules, Calif.), equilibrated in a solution of 1 mM potassium phosphate, 10 mM Tris, and 5 mM DTT (pH 7.5) at room temperature. 1 ml of the dialyzed cell lysate supernate was diluted to 10 ml with a solution of 1 mM potassium phosphate, 10 mM Tris, and 5 mM DTT (pH 7.5) at room temperature and this solution then applied to the column. The column was washed with 20 ml of the buffer used for dilution of the cell lysate supernate and then the methionine sulfoxide reductase eluted using a 1–100 mM linear gradient of potassium phosphate in 10 mM Tris and 5 mM DTT (pH 7.5) while collecting fractions. The fractions containing the methionine sulfoxide reductase are those which are collected at or just after the salt in the elution solution begins to increase due to the gradient of potassium phosphate. Those fractions which have significant amounts of the enzyme are identified by SDS-PAGE electrophoresis of samples of the fractions. Those fractions which are found to contain the enzyme are identified by the fact that they predominantly contain the protein which is found to be overproduced when the gene encoding the enzyme is over-expressed in *E. coli* as described in Example 2. The fractions containing the enzyme were then pooled to form the hydroxyapatite pool.

The hydroxyapatite pool was applied to a Q SEPHAROSE FAST FLOW resin-packed column (Pharmacia) equilibrated with 20 mM Tris, 5 mM DTT, and 5 mM EDTA (pH 7.5). The enzyme was eluted from the column by application of a 0 to 0.75 M NaCl linear gradient in 20 mM Tris, 5 mM DTT, and 5 mM EDTA solution. Fractions were collected. The fractions were sampled and analyzed by SDS-PAGE electrophoresis. Those fractions found to contain the enzyme were identified as described above. The fractions which contained the MSR enzyme and only very small amounts of other proteins were then pooled to form the final enzyme pool. The protein species in this pool of enzymes is predominantly the peptide methionine sulfoxide reductase enzyme of *E. coli*. This pool of MSR enzymes was used in the following Examples.

Example 4

Preparation of NBD-modified Oxidized Dithiothreitol (mDTT)

NBD-hexanoic acid (50 mg) was combined with trans-1, 2-dithiane-4,5-diol (78 mg), dicyclohexylcarbodiimide (38 mg) and 4-dimethylaminopyridine (2 mg) in dichloromethane (10 mL) and dimethylformamide (1 mL) (Sigma) and stirred under argon for 16 hours. The reaction was filtered to remove N,N-dicyclohexyl urea. The filtrate was diluted with dichloromethane and washed with water (3×35 mL), 5% acetic acid (3×50 mL) and again with water (3×50 mL), and dried over $Na_2SO_4$. The solvent was removed under vacuum and the product purified by silica gel chromatography. The product can be identified by NMR ($CDCl_3$, 360 MHz): 8.5 ppm (1H, d, J=8.7 Hz, NBD—H); 6.4 (1H, br s, N—H); 6.18 (1H, d, J=8.7 Hz, NBD—H); 4.9 (1H, d of t, RO—C$\underline{H}$); 3.82 (1H, d of t, HO—C$\underline{H}$); 3.5–2.9 (m); 2.44 (21H, t, N—C$\underline{H}_2$); 2.0–1.0 (m).

Example 5

Preparation of NBD-modified Reduced Dithiothreitol (mDTT)

NBD-modified oxidized DTT made as described in Example 4 was dissolved in methanol to give a solution with an absorbance equivalent to 4 at 465 nm. One ml of this solution was added to 9 ml of 1 M Tris buffer and 100 mM DTT (pH 8.5) and the mixture incubated at room temperature for more than 4 hours. The formation of NBD-modified reduced DTT in the reaction can be confirmed by spotting 0.2 μl of the reaction mix on a 20 cm×20 cm silica TLC (Sigma Chem. Co., St. Louis, Mo.) plate which does not contain a fluorescent indicator, along with 0.1 μl of the methanol solution of NBD-modified oxidized DTT. The plate was allowed to air dry and then developed in a chromatography tank containing 2.5% methanol and 97.5% methylene chloride. The NBD-modified reduced DTT material appears as a fluorescent species which migrates approximately twice as rapidly as the oxidized species. Under the conditions given here, the conversion of NBD-modified oxidized DTT to NBD-modified reduced DTT was essentially quantitative.

To separate the small amount of the NBD-modified oxidized DTT remaining in the mixture from the NBD-modified reduced DTT, the reaction mixture was subjected to reverse phase chromatography using a BECKMAN Model 344 Liquid Chromatography System equipped with a LICHROMSORB RP8 (5 μm) column (BECKMAN Instruments, Columbia, Md.). The system was run using a flow rate 0.5 ml/minute with the detector set to monitor the absorbance of the eluting solvent at 465 nm. The material applied was eluted from the column by application of a linear gradient from 0 to 65% acetonitrile in 0.1% trifluoracetic acid. Fractions of the eluted solvent were collected every 30 seconds and analyzed by TLC as described above. The fractions containing reduced species were found to elute approximately 1.5 minutes prior to the elution of the oxidized species. The fractions containing the NBD-modified reduced DTT species were pooled. The material in this pool was dried in a speed vac and re-dissolved in a sufficient amount of deionized water to produce a solution having an OD of 1.0 at 465 nm versus water.

Example 6

Use of NBD-Modified Reduced DTT to Support the Reaction of Methionine Sulfoxide Reductase with Methionine Sulfoxide A labeled methionine sulfoxide reagent was produced by dissolving methionine sulfoxide (Sigma) to 10 mg/ml in 50 mM sodium borate (pH 9.0) and adding 25 mg of succinimidyl 6-(7-nitrobenz-2-oxa-1,3-diazol-4-yl) aminohexanoate (Molecular Probes, Eugene, Oreg., Product Number S1167) to 2 ml of the amino acid solution. In addition to this reaction, a control reaction was produced which contained all of the reagents listed above with the exception of the methionine sulfoxide. 1 μl of both of these solutions were immediately spotted on a silica gel TLC plate without fluorescent indicator and allowed to air dry. The solutions were then incubated at room temperature with gentle agitation for two hours. After the two hour incubation, the solutions were again spotted on the TLC plate, the spots were air dried and the plate was developed in 80% chloroform, 19% methanol, and 1% acetic acid. The reaction with the methionine sulfoxide was seen to contain a new yellow-colored species which migrated with a mobility of approximately 0.2 versus the solvent front under these conditions.

In order to purify the new species, preparative TLC was performed by spotting samples of the reaction mixture completely across several 20 cm×20 cm TLC plates. The plates were then developed and the region of the plates containing the new yellow species were removed from the plates by scraping with a fresh razor blade. The colored compound was eluted from the silica gel by washing the silica with methanol. The methanol was then dried and the product dissolved in deionized water. This material was NBD-Modified methionine sulfoxide.

NBD-Modified methionine was produced as given above with the exception that L-methionine (Sigma) was used in place of methionine sulfoxide. The material was purified as given above. Under the TLC conditions given above, the NBD-methionine had a relative mobility of approximately 0.6 versus the solvent front. Incubation of the NBD-methionine isolated in water for extended periods of time in contact with air generated a new species with the mobility of the NBD-methionine sulfoxide product discussed above. These data and others indicate that these reactions produced the expected products.

Reactions of the NBD-methionine sulfoxide were prepared as follows: Reaction 1: 200 mM Tris HCl, pH 7.5; 0.25 mM DTT, and 0.5 μg of NBD-labeled methionine sulfoxide (concentration determined using a molar extinction coefficient of 22,000 for the NBD moiety attached to the amino acid), total reaction volume of 50 μl. Reaction 2: As in Reaction 1, but in addition contained 0.9 μg of methionine sulfoxide reductase (produced as described above and having a concentration of 0.4 mg protein/ml). Reaction 3: As in Reaction 2, but in addition contained 50 nM thioredoxin. Reaction 4: As in Reaction 1, but in addition contained 6 μM NBD-modified reduced DTT and no unlabeled DTT. Reaction 5: As in Reaction 4, but in addition contained 0.9 μg methionine sulfoxide reductase. Reaction 6: As in Reaction 4, but in addition contained 50 nM thioredoxin.

Figure 1:
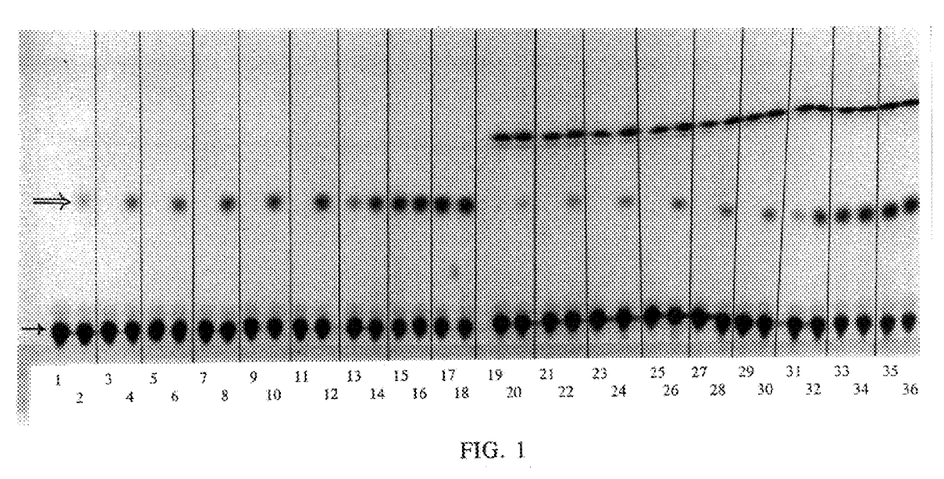

The reactions were sampled immediately upon addition of the final reagent by removal of a 0.5 μl of the reaction mixture, spotting the sample on a silica gel TLC plate and allowing the sample to air dry. The solutions were again sampled after 1, 2, 3, 4, and 5 minutes of incubation at room temperature. All of the sample spots were allowed to air dry and the plate developed using a solution of 80% chloroform, 19% methanol, and 1% acetic acid. Separate experiments were performed to determine the mobility of the NBD-modified oxidized DTT and the NBD-modified reduced DTT under the same conditions. The experiments indicated that the two species migrate with a relative mobility of greater than 0.95 under these conditions and that the mobility differential between the species was too small to allow effective separation of the species. When the solvent front had moved approximately 10 cm up the plate, the plate was removed from the chromatography tank and scanned using a Molecular Dynamics FLUOROIMAGER brand fluorescence detection device. FIG. 1 shows a print-out of the image detected for fluorescent materials on the plate.

As shown in FIG. 1, the NBD-methionine sulfoxide was not reduced in the presence of either DTT or NBD-modified reduced DTT in the absence of the enzyme methionine sulfoxide reductase (see lanes for Reactions 1 and 4 in FIG. 1). Both DTT and NBD-modified reduced DTT supported the enzymatic reduction of the NBD-methionine sulfoxide in a time dependent manner (see lanes for Reactions 2 and 5 samples in FIG. 1) However, the addition of thioredoxin greatly increased the rate of formation of NBD-methionine in these reactions using either reducing reagent (see lanes for Reactions 3 and 6 in FIG. 1).

Independent studies indicated that the production of NBD-methionine in Reactions 3 and 6 is absolutely dependent upon the addition of methionine sulfoxide reductase under these conditions. Analogous studies utilizing solely thioredoxin at the above concentration showed that thioredoxin only very, very slowly produced NBD-methionine under these conditions. Thus, the presence of both thioredoxin and NBD-modified reduced DTT had a very strong synergistic effect that results in the rapid production of reduced methionine sulfoxide by the enzyme, an effect not previously reported for such an enzyme.

Example 7

Use of N-Ethyl Maleimide as a Stop Reagent for Reactions of Methionine Sulfoxide Reductase Reactions carried out using the NBD-modified reduced DTT without any additions except buffer indicated that a significant percentage of the reagent would oxidize during the course of the reaction if the reaction were carried out under the conditions given in Example 6. In addition, this non-enzymatic oxidation would continue to proceed until all of the modified DTT reagent had been oxidized. This continued background oxidation would make accurate quantitation of low amounts of methionine sulfoxide using such reactions difficult due to the large amount of background oxidation formed and the need to rapidly process the samples following completion of the reactions. The non-enzymatic oxidation is probably due to atmospheric oxygen in the reaction containers and thus could be eliminated by performing the reactions under an inert atmosphere or under very reduced pressure conditions. However, the sensitivity of the reaction to further oxidation over time would compel users to rapidly analyze the reaction products. Since not all separation systems allow rapid and simultaneous analysis of the reaction products, it was decided to identify stop reagents which would transform the NBD-modified reduced DTT into a chemical species which would be time stable under most storage conditions. Experiments were performed which showed that incubating the NBD-modified oxidized DTT under the above conditions did not have any degradative effect on the oxidized reagent. Thus, experiments were conducted to find a stop reagent to prevent background oxidation of the NBD-modified reduced DTT.

The scientific literature describes several compounds which react with sulfhydryl groups to stabilize them against oxidation. Such reagents include N-ethyl maleimide (NEM), iodoacetic acid, iodoacetamide, and several others. It was decided to determine if any of these reagents could be added to reactions assembled as in Example 6 to stop further oxidation reactions and to prevent complete oxidation of the NBD-modified reduced DTT over time.

The following reactions were assembled: Reaction 1: 200 mM Tris HCl, pH 7.5; 250 pmole of acetyl methionine sulfoxide (Sigma), and 6 $\mu$M NBD-modified reduced DTT in a total reaction volume of 50 $\mu$l. Reaction 2: as in Reaction 1, but including 50 nM thioredoxin. Reaction 3: as in Reaction 1, but including 0.9 $\mu$g of methionine sulfoxide reductase (produced as described above and having a concentration of 0.4 mg protein/ml). Reaction 4: as in Reaction 3, but including 50 nM thioredoxin.

All reactions were incubated at 22° C. for 6 minutes. After this incubation, one $\mu$l of each reaction was spotted on a silica gel TLC plate without fluorescent indicator. Immediately after spotting the TLC plate with the reaction, 25 $\mu$l of the reaction mix was added to 25 $\mu$l of 10 mM N-ethyl maleimide (NEM) and the solution was mixed for 5 seconds. 2 $\mu$l of this new solution was then spotted on the TLC plate and all spots were allowed to air dry. A sample of a solution containing both NBD-modified reduced DTT and NBD-modified oxidized DTT was also spotted on the plate and air dried to provide reference standards for these compounds. The plate was then developed in a TLC tank using a solution of 2.5% methanol and 97.5% methylene chloride as a developing solvent. After the solvent front had reached a height of approximately 8 cm, the plate was removed, air dried and the fluorescent species on the plate were examined using the Molecular Dynamics FLUOROIMAGER brand fluorescence detection device. The results are shown in FIG. 2.

Figure 2:
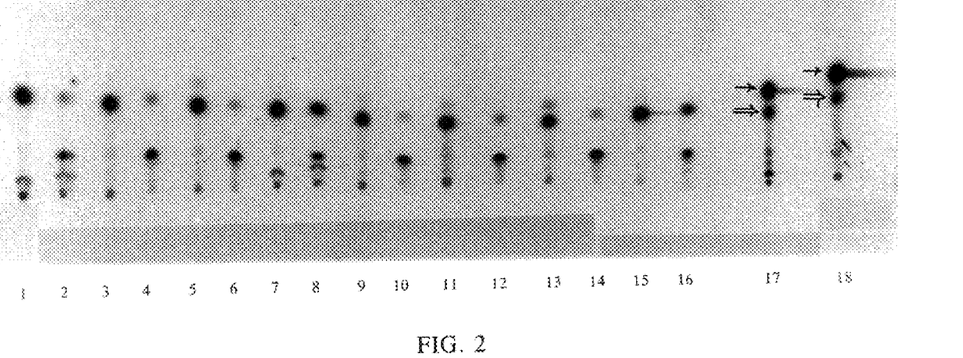

As shown in FIG. 2, the addition of NEM to the reactions results in the formation of a new species which has a mobility far below that of the NBD-modified reduced DTT and NBD-modified oxidized DTT. This result agrees with other experiments which indicated that the mobility of the NEM reaction product with the NBD-modified reduced DTT had a mobility about one-third that of the NBD-modified oxidized DTT.

The data indicate that acetyl methionine sulfoxide can be detected using the conditions given. This agrees with the scientific literature that this reagent is a substrate for peptide methionine sulfoxide reductase. In addition, these data again show that the reaction catalyzed by methionine sulfoxide reductase using the NBD-modified reduced DTT is greatly stimulated by the addition of thioredoxin. However, this effect can only be clearly shown for reactions with these levels of acetyl methionine sulfoxide when the reaction products are reacted with NEM since the oxidation of the NBD-modified reduced DTT which occurs following spotting of the material on the TLC plate and possibly during the initial running of the plate can mask the effect.

These reactions were frozen at −10° C. for six days and then reanalyzed as indicated above. The amount of the different NBD-modified species in the NEM-reacted samples was found to be equal to that seen immediately following reaction with NEM. Thus, the reaction products of NEM are relatively stable and can be analyzed several days following reaction.

Samples of the NBD-modified oxidized DTT, NBD-modified reduced DTT and NEM-reacted, NBD-modified reduced DTT were fractionated using high pressure liquid chromatography as described in Example 5. These data indicated that the NEM-reacted, NBD-modified reduced DTT had a retention time approximately 2 minutes later than that of the NBD-modified oxidized DTT. Thus, the reactions can be analyzed using HPLC fractionation of the species, if desired.

Example 8

Quantitation of Methionine Sulfoxide in Three Different Substrates Using NBD-Modified Reduced DTT and Methionine Sulfoxide Reductase With conditions defined to stabilize the reaction products following incubation of solutions of methionine sulfoxide and the NBD-modified reduced DTT, quantitation of the amount of NBD-modified oxidized DTT produced in such reactions upon addition of various amounts of substrates containing methionine sulfoxide were performed. The scientific literature indicated that acetyl methionine sulfoxide, met-(O)-enkephalin, and met-(O)-arg-enkephalin were substrates for methionine sulfoxide reductase.

Duplicate reactions were assembled containing 0, 50, 100, 200, 400, or 600 pmoles of these substrates in addition to 200 mM Tris-Cl (pH 7.5) and NBD-modified reduced DTT in a 50 μl reaction volume. The met-(O)-enkephalin and met-(O)-arg-enkephalin were both obtained from Bachem Biosciences Inc. (King of Prussia, Pa.). Incubation was performed at 22° C. for 8 minutes followed by addition of 50 μl of 10 mM NEM to stop the reaction and to stabilize the NBD-modified products.

2 μl from each reaction was spotted on a silica gel TLC plate without fluorescent indicator and the spots were allowed to air dry. The plate was developed and analyzed as described in Example 7.

Figure 3:
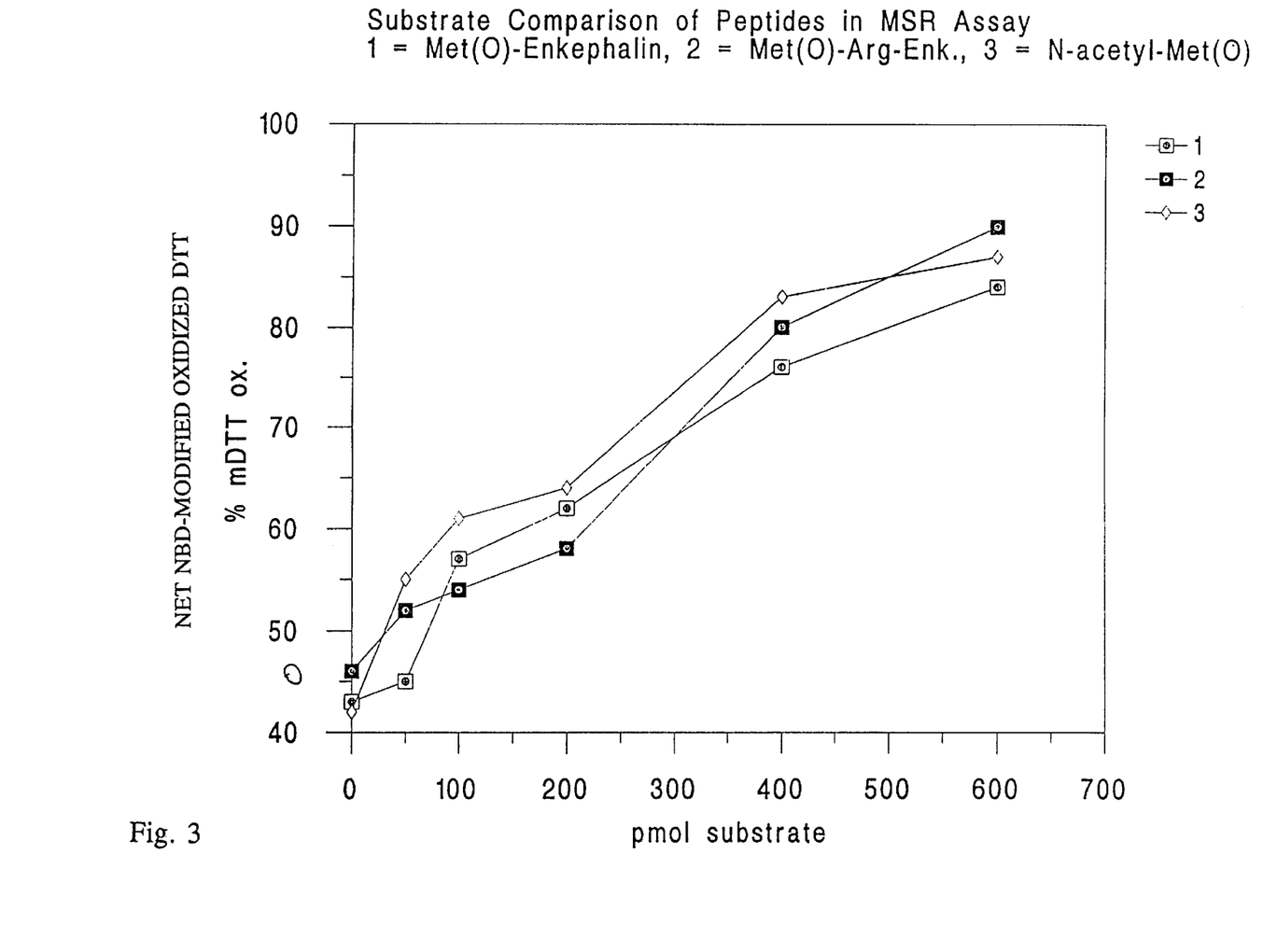
FIG. 3: A graph of the percent net NBD-modified oxidized DTT determined in the reactions described in Example 8 versus the amount of methionine sulfoxide-containing substrate added is shown. The symbols for the various substrates are: diamonds; N-acetyl methionine sulfoxide; dark squares with grey circles met-(O)-Arg enkephalin; white squares with grey circles; met-(O)-enkephalin.

The net amount of NBD-modified oxidized DTT produced was determined from the scanned image using the quantitation method given with the Molecular Dynamics FLUOROIMAGER brand fluororescence detection device. These values were then plotted versus the amount of methionine sulfoxide present in the reactions to generate the graph shown in FIG. 3. As can be seen from FIG. 3, the net amount of NBD-modified oxidized DTT measured increased as the amount of substrate containing methionine sulfoxide was increased in a very similar fashion for each of the three substrates used. These data indicate that the assay methodology described above is able to measure methionine sulfoxide in a wide range of substrates.

Example 9

Comparison of the Amount of Methionine Sulfoxide Detected in a Sample When the Products of the Methionine Sulfoxide Reductase Reaction are Analyzed by TLC versus HPLC Reactions were assembled containing various concentrations of acetyl methionine sulfoxide for analysis using methionine sulfoxide reductase as described in Example 8 except that triplicate reactions were assembled at each substrate concentration. Following the addition of the 10 mM NEM solution to stop the reaction, 2 μl of each reaction solution was spotted on a silica gel TLC plate and the spots were allowed to air dry. The plate was developed and scanned and the amount of NBD-modified oxidized DTT and NEM-reacted, NBD-modified reduced DTT was determined as described in Example 8. These data were used to determine the percentage of the modified DTT which was oxidized in each reaction. The net percentage of the NBD-modified oxidized DTT was determined for each reaction.

The remaining amount of each solution was analyzed by HPLC using fractionation conditions as described in Example 5. The species detected under these conditions eluted at the expected retention times for the NBD-modified oxidized DTT and the NEM-modified, NBD-modified reduced DTT. The respective peak heights on the chart paper used to record the absorbance of these two species were measured and used to determine the percentage of the total peak height of the two species which was due to NEM-reacted, NBD-modified DTT in order to estimate the amount of net NBD-modified oxidized DTT that was produced in each reaction.

A linear relationship was found when the net percent of NBD-modified oxidized DTT which was found in the reactions were graphed versus the amount of acetyl methionine sulfoxide added to the reactions using the data obtained from either quantitation method. The correlation between the average net percentage of NBD modified oxidized DTT measured by both methods in these reactions was then compared and found to be nearly identical. These data indicate that either method can be used to quantitate the products of the reaction for determination of the amount of methionine sulfoxide present in a sample.

Example 10

Quenching of the Fluorescence of NBD-Modified Reduced DTT by Divalent Metal Salts The emission spectra of NBD-modified reduced DTT was measured using a SPEX® Fluorolog-2 Model 122XI spectrofluometer. The excitation wavelength used was 480 nm and the emission was scanned from 490 nm–700 nm. The stock solution of NBD-modified reduced DTT used in Example 7 was diluted 1:1000 into water and the emission spectra was measured. A solution of 1 M zinc chloride was then diluted into the sample to a final concentration of 10 mM and the emission spectra was again scanned. The drop in emission obtained by addition of various other salts was then determined as described above and the percent of fluorescence remaining was determined and is presented in graphic form in FIG. 4.

Figure 4:
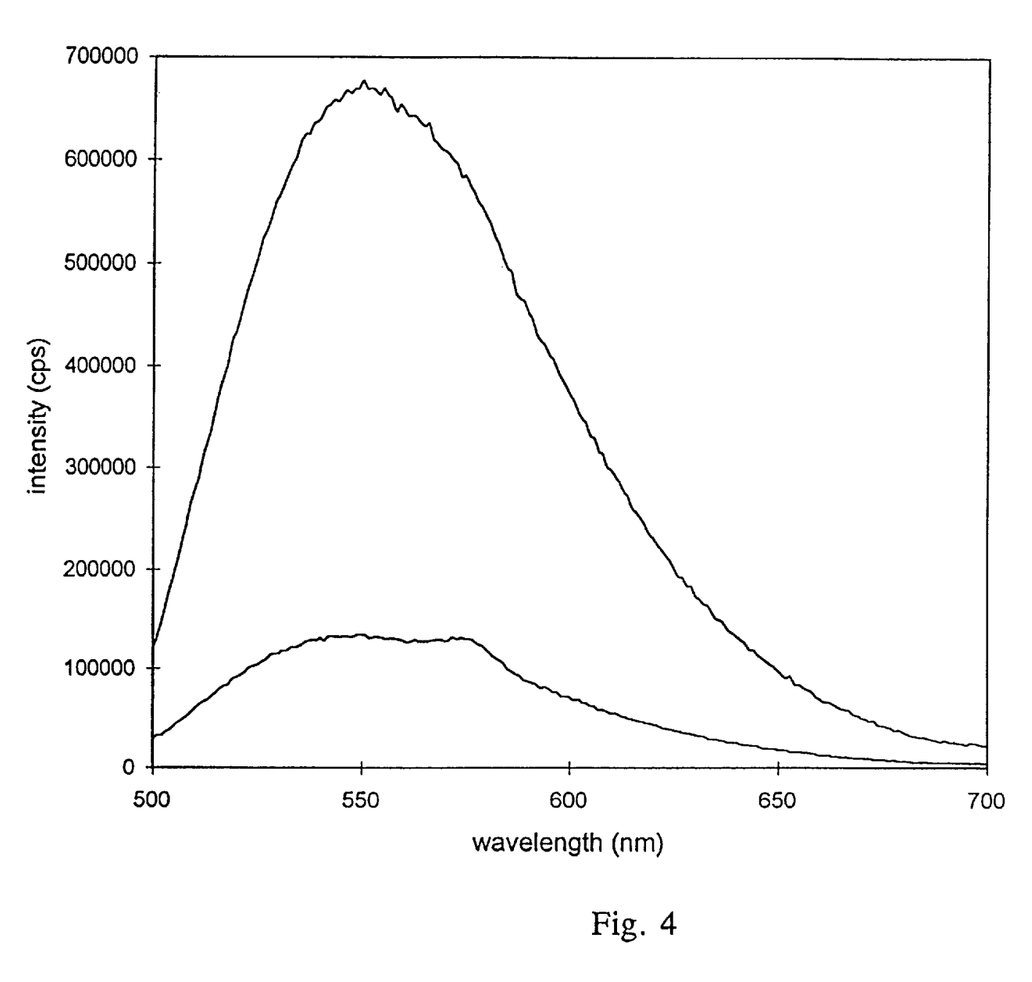
FIG. 4: A graph depicting fluorescence of NBD-modified reduced DTT in the presence and absence of divalent metal ion is shown. The relative fluorescence of a solution of NBD-modified reduced DTT in the presence and absence of 1 mM zinc chloride over various wavelengths measured as described in Example 10 is shown. The upper curve represents the relative fluorescence of the solution in the absence of the metal ion; the lower curve, the relative fluorescence in the presence of the metal ion.

The data depicted in FIG. 4 indicate that divalent metal ions effectively quench the fluorescence of the reduced form of the modified DTT reagent. The effect of zinc chloride on the oxidized form of the reagent was also studied. Zinc chloride was found to have a much smaller effect on oxidized form of the reagent than was seen for the reduced reagent.

Example 11

Use of NBD-Modified Reduced DTT to Measure Disulfide Bonds in a Protein

The NBD-modified reduced DTT can be used to detect the presence of disulfide bonds in a protein and estimate the number of such bonds per polypeptide chain. However, as the reaction of the reagent with proteins might take significantly longer periods of time than the five to ten minute incubations needed for methionine sulfoxide measurement, the reactions are preferably performed either in vacuum or under an inert atmosphere of nitrogen or argon in a sample container that can be loaded and sampled under vacuum. Such vials are commercially available from many sources and usually are sealed from the atmosphere by use of a rubber septum.

To perform such analysis, it is important to place the protein under conditions which will expose the disulfide bonds. For instance, a high concentration of a denaturant such as urea and guanidine will serve to make the disulfide bonds available for reaction. Thus, to measure such bonds, a reaction buffer of 100 mM Tris-Cl (pH 8.0) and 8 M urea was prepared and deaerated under vacuum.

A solution of protein having a concentration of 1 nmole of polypeptide in 10 μl of buffer, was gently deaerated under vacuum. A volume of the protein solution was added to 100 μl reaction buffer under vacuum. If the solution contains a reducing reagent such as DTT or β-mercaptoethanol, the solution must be extensively dialyzed to remove these substances before the reaction is performed.

An NBD-modified reduced DTT solution, having a concentration of 5 nmole per 15 μl of solution, was deaerated under vacuum. 15 μl of the solution was added to the protein solution under vacuum. A reaction blank and reaction standards were also assembled under vacuum as described above. The reaction blank contains all the materials in the reaction given above except that 10 μl of deaerated buffer is used in the place of the protein sample. The standard reactions use the same materials as the test reaction given above except that one standard reaction is made using a solution of 1 nmole of insulin in deaerated buffer as a sample and a second standard contains 1 nmole of chicken lysozyme as a standard.

The reactions are allowed to incubate at room temperature. To test the reactions 10–20 μl of each reaction solution was withdrawn through the septum using a syringe. The withdrawn solution was added immediately to an equal volume of 10 mM NEM and mixed. The NEM-containing solution was then spotted on a TLC plate and the percent of NBD-modified oxidized DTT in the samples determined. The amount found in the reaction blank was subtracted from that found in the test samples. If significantly more NBD-modified oxidized DTT is found in the sample reaction, the sample is determined to have contained disulfide bonds.

If the number of disulfide bonds per polypeptide chain is to be determined, the percent of NBD-modified oxidized DTT found per 1 nmole of lysozyme and insulin is determined. Since insulin is known to have two disulfide bonds and lysozyme is known to have four disulfide bonds, the values of the percent NBD-modified oxidized DTT is divided by 2 and 4 respectively to determine the percent of NBD-modified oxidized DTT expected per disulfide bond in a 1 nano-mole sample. This value is divided into the net percentage NBD-modified oxidized DTT found in the unknown sample to estimate the number of disulfide bonds present per polypeptide chain.

It is understood that the invention is not confined to the embodiments herein illustrated and described, but embraces all such modified forms thereof as come within the scope of the attached claims.

wherein methionine sulfoxide in the sample is reduced and a proportional amount of the reducing reagent is oxidized; and then (b) quantifying the amount of oxidized reducing reagent.

2. The method according to claim 1, further comprising the step of: subsequent to step (a) and prior to step (b), adding a stop reagent to the sample.

3. The method according to claim 2, wherein a stop reagent selected from the group consisting of bromoacetic acid; 5,5'-dithionitro-bis(2-nitrobenzoic) acid; and N-ethyl maleimide is added to the sample.

4. The method according to claim 1, wherein in step (a) the reducing reagent is selected from the group consisting of dithiothreitol and β-mercaptoethanol, and the covalently-linked reporter tag is a fluorophore.

5. A method to determine the amount of methionine sulfoxide in a peptide or protein-containing sample, the method comprising the steps of:

(a) contacting the sample with a methionine reductase in the presence of a reducing agent comprising dithiothreitol covalently linked to 6-(7-nitrobenz-2-oxa-1,3-diazol-4-yl) aminohexanoate, whereby methionine sulfoxide in the sample is reduced and a proportional amount of the reducing agent is oxidized; and then (b) quantifying the amount of oxidized reducing agent.

6. The method according to claim 4, further comprising the step of: subsequent to step (a) and prior to step (b), adding a metal salt to the sample.

What is claimed is:

1. A method to determine the amount of methionine sulfoxide in a peptide or protein-containing sample, the method comprising the steps of:

(a) contacting the sample with a methionine reductase in the presence of a sulfhydryl group-containing reducing reagent including a covalently-linked reporter tag, 7. The method according to claim 6, wherein a metal salt selected from the group consisting of $FeCl_3$, $MgCl_2$, $MnSO_4$, $NiSO_4$, RbCl, $CuSO_4$, $CuCl_2$, $CoCl_2$, $CsCl_2$, $CaCl_2$, and $ZnCl_2$ is added to the sample.

8. The method according to claim 1, wherein step (a) further comprises contacting the sample with methionine sulfoxide reductase in the presence of thioredoxin.

9. A kit for quantifying methionine sulfoxide in a peptide or protein-containing sample, the kit comprising, in combination:

a methionine sulfoxide reductase enzyme disposed in a first container; and a sulfhydryl group-containing reducing reagent including a covalently-linked reporter tag disposed in a second container.

10. The kit according to claim 9, further comprising:

a stop reagent disposed in a third container.

11. The kit according to claim 10, wherein the reducing reagent is selected from the group consisting of dithiothreitol and β-mercaptoethanol, the covalently-linked reporter tag is a fluorophore, and the stop reagent is N-ethyl maleimide.

12. The kit according to claim 11, wherein the fluorophore is 6-(7-nitrobenz-2-oxa-1,3-diazol-4-yl) aminohexanoate.

13. A composition of matter comprising dithiothreitol covalently linked through at least one of its two hydroxyl moieties to a fluorophore.

14. A compound comprising dithiothreitol covalently linked through at least one of its two hydroxyl moieties to 6-(7-nitrobenz-2-oxa-1,3-diazol-4-yl) aminohexanoate.

* * * * *